US006423323B2

(12) United States Patent
Neubourg

(10) Patent No.: US 6,423,323 B2
(45) Date of Patent: Jul. 23, 2002

(54) FOAM SKIN CREAM, USES OF THE FOAM SKIN PROTECTION CREAM AND A PROCESS FOR ITS PREPARATION

(75) Inventor: Fritz Neubourg, Emsdetten (DE)

(73) Assignee: Stephanie Neubourg, Emsdetten (DE)

( * ) Notice: Subject to any disclaimer, the term of this patent is extended or adjusted under 35 U.S.C. 154(b) by 13 days.

(21) Appl. No.: 09/485,930

(22) PCT Filed: Aug. 18, 1998

(86) PCT No.: PCT/EP98/05232
§ 371 (c)(1),
(2), (4) Date: Feb. 18, 2000

(87) PCT Pub. No.: WO99/08649
PCT Pub. Date: Feb. 25, 1999

(30) Foreign Application Priority Data

Aug. 18, 1997 (DE) .......................... 197 35 591

(51) Int. Cl.$^7$ ........................... A61K 6/00; A61K 7/08;
A61K 9/14; A61K 31/12; C11D 3/50
(52) U.S. Cl. .................... 424/401; 424/70.24; 424/489;
510/101; 514/680
(58) Field of Search .............................. 424/70.24, 489,
424/401; 510/101; 514/680

(56) References Cited

U.S. PATENT DOCUMENTS

| 2,968,628 A | | 1/1961 | Reed |
| 4,551,480 A | * | 11/1985 | Stiefel et al. ............... 514/680 |
| 4,661,340 A | | 4/1987 | Nagy Nee Krisfalussy et al. |
| 5,525,588 A | * | 6/1996 | Michetti ..................... 512/4 |
| 5,534,265 A | * | 7/1996 | Fowler et al. ............... 424/489 |
| 5,540,853 A | * | 7/1996 | Trinh et al. ................. 510/101 |
| 5,616,746 A | * | 4/1997 | Mahieu et al. ............... 554/66 |
| 5,621,012 A | * | 4/1997 | Schonrock et al. ......... 514/629 |
| 5,653,970 A | * | 8/1997 | Vermeer .................... 424/70.24 |

FOREIGN PATENT DOCUMENTS

| DE | 33 30628 | 3/1985 |
| DE | 4431 365 | 3/1995 |
| EP | 0194097 | 9/1986 |
| EP | 0 257 336 | 3/1988 |
| EP | 05 98 412 A2 | 5/1994 |
| FR | 2217.405 | 9/1974 |

OTHER PUBLICATIONS

Griffith, H. Winter; Vitamins, Herbs, Minerals & Supplements The Complete Guide; 1988, MJF Books; pp. 229, 247, 444, 460.*

Ziolkowsky, "Moderne Aerosolschaüme in der Kosmetik" Seifen–Ole–Fette–Wachse, vol. 112, No. 13, Aug. 1986, pp. 427–429.

* cited by examiner

Primary Examiner—Michael G. Hartley
Assistant Examiner—Michael A. Willis
(74) Attorney, Agent, or Firm—Jacobson Holman, PLLC

(57) ABSTRACT

A foam skin cream can be obtained by preparing a phase I by melting at 75° C. a mixture containing fatty acids, especially $C_{12}$–$C_{22}$ fatty acids, optionally unsaturated and/or polyunsaturated fatty acids, emulsifiers, coemulsifiers, such as triceteareth-4-phosphate, followed by metering it with stirring to a phase II temperature-controlled at 75° C. obtained from an aqueous mixture containing moisturizers, such as propylene glycol and/or polyhydric alcohols, especially glycerol, emulsifiers, such as alkyl sarcosinates, and skin care additives, such as allantoin;

wherein homogeneous mixing of phases I and II is provided and said metering is performed at a temperature of 75° C.;

after the metered addition, the temperature is maintained at 75° C. for a period of between 5 and 20 minutes; whereupon the temperature of the thus obtained mixture is lowered to a temperature of between 30 and 40° C. with constant stirring;

the pH value is adjusted to from 7.6 to 8.2, preferably with a skin-compatible basic organic compound, and the mixture obtained is filled into dosage forms with the addition of a propellant.

23 Claims, No Drawings

FOAM SKIN CREAM, USES OF THE FOAM SKIN PROTECTION CREAM AND A PROCESS FOR ITS PREPARATION

This application is a 371 of PCT/EP/98/05232 filed Aug. 18, 1998

The present invention relates to a foam skin cream, uses of the foam skin protection cream and a process for its preparation.

The galenic principle of an emulsoid two-phase system having lipophilic or hydrophobic components and, on the other hand, hydrophilic components has been known for the production of foam preparations for skin care. The application of these foam preparations to the treated skin forms a two-dimensional two-phase network, the hydrophilic components bind to the keratin of the horny layer and enable the evaporation of sweat while the lipophilic components inhibit the permeation of moisture (including the penetrated sweat) on the skin surface. As the foam, in contrast to other creams building a barrier, is absorbed in less than a minute, does not leave any grease traces on the working materials and prevents heat built-up or even maceration effects from the action of sweat, the foam has enjoyed rapidly growing popularity as a protective agent against occupational action of moisture. Further details about the per se known foam skin creams can be seen, in particular, from "Haut",issue 4, 1992, by R. Rudolph, L. Bade, B. Brüggemann.

In "hautnah derm" 10 (1994), 344–351, B. Kunze reports lipid-containing skin protection foams which are indicated for dry sensitive skin and chronical-rhagadiform eczemas. Ingredients are also disclosed therein. The skin protection foams described therein are protective against a lot of occupational noxious matters, such as acid permanent waving liquids in the hairdresser's trade, lyes, oils, disinfectants, cleaning and rinsing agents, but also against water, moisture, sweat, feces, urine and mineral dusts.

EP 0 598 412 also relates to skin protection foams; PTFE is described as an active principle.

DE-C-33 30 628 relates to skin protection and care lotions containing silicone oils, partially neutralized stearic acid, fatty alcohols and their ethoxylated derivatives, ethoxylated wool alcohols, cetyl/stearyl alcohol, vaseline, thickeners and water. The lotions disclosed therein are said to be quickly absorbed without leaving an annoying grease film on the skin for extended periods of time.

Information about emulsifiers which can be employed in skin care agents are found in DE-A-195 42 572. This reference suggests emulsifiers which contain from 43 to 90% by weight of alkyl and/or alkenyl oligoglycosides and from 10 to 57% by weight of fatty alcohols. These emulsifiers are particularly suitable for the preparation of highly viscous, sensorily light oil-in-water emulsions having a long shelf life. The German utility model DE-U9308050 relates to a skin protection foam used against skin-aggressive agents. This foam consists of an aqueous emulsion containing fatty acid esters with good skin compatibility for the production of a moisture-permeable film, polyhydric alcohol for stably dispersing the active agents and controlling the humidity of the film, emulsifiers for improving foam stability, surfactants for reducing the surface tension and optionally neutralizing agents for resins and emulsifiers. Gaseous hydrocarbons may be used as propellants, for example, propane, butane or isobutane and mixtures thereof. However, the foams described do not contain any free fatty acids.

Aerosoles are complicated physical-chemical structures which do not form under arbitrary circumstances. In Particular, a special balance between the foam-forming components is important. Slight shifts in the composition may already result in a collapse of the foam; thus, a formulation of per se active substances may not be capable of being formulated as a foam without further provisions.

Especially in occupational applications, skin creams are often found unpleasant because the "fatting" components remain too long on the skin and lead to annoying finger traces or generally to an unpleasant feeling. This has been remedied to some extent by the per se known skin foams since they help preventing or reducing overload of the skin with the fatting matters. Nevertheless, it is desirable to find even more acceptance by the user, especially in the long-term use of skin protection agents.

It has been the object of the present invention to extend the application range of skin protection foams by providing a formulation which is highly accepted by the user, the admixture of a wide variety of other substances being allowed without destroying the aerosol employed or deteriorating the properties of the aerosol.

The object of the invention is surprisingly achieved by a base formulation of a foam skin cream having the features disclosed and claimed in the present application, including preferred embodiments of the foam skin cream according to the invention, uses of the foam skin cream according to the invention, and a process for preparing the base of a foam skin cream according to the invention.

The foam skin cream according to the invention can be obtained by preparing a phase I by melting at 75° C. a mixture containing fatty acids, especially $C_{12}$–$C_{22}$ fatty acids, optionally unsaturated and/or polyunsaturated fatty acids, emulsifiers, coemulsifiers, such as triceteareth-4-phosphate, followed by metering it with stirring to a phase II temperature-controlled at 75° C. obtained from an aqueous mixture containing moisturizers, such as propylene glycol and/or polyhydric alcohols, especially glycerol, emulsifiers, such as alkyl sarcosinates, and skin care additives, such as allantoin;

wherein homogeneous mixing of phases I and II is provided and said metering is performed at a temperature of 75° C.;

after the metered addition, the temperature is maintained at 75° C. for a period of between 5 and 20 minutes; whereupon the temperature of the thus obtained mixture is lowered to a temperature of between 30 and 40° C. with constant stirring;

the pH value is adjusted to from 7.6 to 8.2, preferably with a skin-compatible basic organic compound, and the mixture obtained is filled into dosage forms with the addition of a propellant.

At the one hand, the product obtainable according to this process can be directly employed as a foam skin cream in the industrial field for the protection from or reduction of the absorption of cancerogenic substances, such as polycyclic aromatic hydrocarbons. This mixture is capable of providing effective protection for persons whose skin has already been exposed to cancerogenic substances, such as polycyclic aromatic hydrocarbons. In addition, the mixture is suitable for providing protection to persons from the action of acids, lyes (not above pH 11), scouring agents and detergents, sweat, urine, stool, rubber gloves, dusts, house dust, machine, drilling and cooling oils, greases, paints/varnishes, gypsum and other substances and chemicals, especially aggressive substances and chemicals.

The foam skin cream according to the invention contains fatty acids, especially $C_{12}$–$C_{22}$ fatty acids, and may optionally additionally contain unsaturated and/or polyunsaturated fatty acids. Useful fatty acids which are saturated include, in particular, the naturally occurring $C_{12}$–$C_{22}$ fatty acids, especially stearic acid and palmitic acid. Myristic acid may also be used. Useful unsaturated fatty acids include, in particular, those having up to three unsaturated bonds in their hydrocarbon chain. Unsaturated fatty acids are found, for example, in fractions of coconut fat. Useful coemulsifiers include per se known coemulsifiers, especially triceteareth-4-phosphate, sodium laureth-4-phosphate or oleth-3 and other lipophilic emulsifiers based on fatty alcohols with a low degree of ethoxylation.

Phase I may additionally contain paraffinum liquidum. Emulsifiers to be used in phase I may include those based on fatty alcohols and those based on partial esters of fatty acids. Particularly preferred fatty alcohols include cetearyl alcohol. Glyceryl stearate, for example, may be employed as a partial ester of a fatty acid.

The moisturizers to be used in phase II include, in particular, propylene glycol and/or polyhydric alcohols, such as glycerol. As particular emulsifiers to be used in phase II, there may be mentioned alkyl sarcosinates, such as lauroyl, lauryl, cetyl sarcosinates.

The mixture obtainable according to claim 1 also serves as a base for other foam skin creams which may be employed in a wide range of applications for protecting the skin and alleviating dermatological dysfunctions.

If desired, one or more preservatives may be added to the foam skin cream according to the invention. In particular, substances such as methyldibromoglutaronitrile and/or phenoxyethanol have proven to be suitable preservatives. These substances may be added in amounts of from 0.01 to 1% by weight.

Preferably, the emulsifiers, fatty acids, coemulsifiers, moisturizers and skin care agents, especially allantoin, panthenol etc., are used in the following amounts:

from 4 to 15% by weight of oil-in-water emulsifier;

from 1 to 10% by weight of fatty acid, especially from 4 to 7% by weight, preferably from 4.5 to 6% by weight;

from 0.4 to 2.3% by weight of coemulsifier;

from 1 to 10% by weight of moisturizer;

from 0.05 to 1% by weight of skin care agent; and water as the balance to make 100% by weight.

A preferable foam skin cream according to the invention contains:

from 1 to 3% by weight of glyceryl stearate;

from 3 to 6% by weight of cetearyl alcohol;

from 4 to 6% by weight of stearic acid;

from 0.5 to 2% by weight of paraffin;

from 0.4 to 2.3% by weight of triceteareth-4-phosphate;

from 1.5 to 4% by weight of propylene glycol;

from 1.3 to 4.2% by weight of glycerol;

from 1 to 3% by weight of cetyl sarcosinate;

from 0.05 to 1% by weight of allantoin; and water as the balance to make 100% by weight.

In another preferred embodiment, the foam skin cream according to the invention additionally contains a silicone-containing substance, such as dimethicone. This substance is added to phase I. Preferably, it is present in amounts of from 0.05 to 1% by weight.

In addition, the foam skin cream according to the invention may additionally contain one or more refatting substances in phase I, such as decyl oleate, isohexadecane, stearic acid glycol ester, coconut fatty acid ethanolamide, corn oil, peanut oil, almond oil, sesame oil, olive oil, jojoba oil, soybean oil, wool wax alcohols, paraffin, medium-chain triglycerides, oleic acid oleyl esters, white petrolatum, macrogol-glycerol hydroxystearate, hydrogenated castor oil, castor oil from *Ricinus communis*, avocado oil, wheat germ oil, palmitic acid isopropyl ester, cetyl palmitate, myristic acid myristyl ester and/or octyidodecanol.

In particular, the foam skin cream contains amounts of from 0.5 to 2% by weight of decyl oleate and/or from 0.5 to 2% by weight of octyldecanol, or another of the refatting substances mentioned, if the product is to be used for normal skin. The total amount of refatting substances is to be such that the skin protection foam is not destroyed. An amount of about 4% by weight of refatting substances is sufficient for normal to slightly dry skin. If dry skin is to be treated with the foam skin cream according to the invention, amounts of from 3 to 6% by weight of a component of the refatting substances, such as, in particular, decyl oleate. and/or octyidecanol, are recommendable. If more than one component is used, the total amount of refatting components is to be about 12% at most for slightly dry skin. If even more severely dry skin is treated, the amount of refatting substances is from about 6 to 9% by weight if a component such as decyl oleate is used, and from 6 to 9% by weight if octyidecanol is used. The amount of refatting substance may then be up to 20% by weight.

Like the products without silicone-containing substances, the latter foam skin creams are suitable for the care and protection of the skin, especially from aggressive substances, such as scouring agents and detergents, sweat, urine, stool, rubber gloves, dusts, house dust, machine, drilling and cooling oils, greases, paints/varnishes, gypsum and other substances and chemicals, especially aggressive substances and chemicals.

The foam skin creams are also suitable for the treatment or alleviation of dermatological diseases. This includes, in particular, dermatological diseases such as allergic contact dermatitis type I and IV, cumulative-subtoxic eczema, toxic-irritative eczema, microbial-dysregulative eczema, atopic dermatitis, atopic palmoplantar eczema, dyshidrosis, hyperhidrosis, contact urticaria, intertriginous eczema in connection with hemorrhoids, various weeping fungal infections, e.g., interdigital mycosis, perleches, psoriasis vulgaris, ulcus cruris, cholinergic urticaria, diaper dermatitis.

It may be indicated to include substances which can increase the moisture content of the skin, in addition to refatting substances. Such hydratizing substances include, in particular, urea, ethoxydiglycol, sodium chloride, magnesium chloride, sorbitol, dexpanthenol, sodium lactate, allantoin, hyaluronic acid, vitamin E, linolenic acid. The amount of those substances can be from 1 to 20% by weight or more of the respective substances, depending on the severity of the disease to be treated. These quantities also apply, in particular, to urea which may also be present in amounts of from 3 to 15% by weight or from 12.5 to 15% by weight. The foam skin cream according to the invention may also be used for psoriasis.

One particularly important field of application concerns the prophylaxis and treatment of diabetic foot. Due to accompanying symptoms of diabetes, diabetics suffer from dry skin which in the course of the diseases favors damage to the extremities, up to an extent where amputation becomes necessary in the case of those having been diabetic for many years. Prophylactic application of skin protection agents which provide an improvement of the skin parameters in diabetics can prevent the development of diabetic foot.

In addition, skin care substances, such as polyunsaturated fatty acids (PUFA), may be added to the foam skin cream according to the invention. These include, in particular, omega-6 fatty acids as known, for example, from evening primrose oil and borage oil. Both synthetic omega-6 fatty acids and those obtained from the mentioned plant extracts may be employed.

Further, there may be used soothing substances, such as chamomile extract, as another fraction which may be admixed with the foam skin cream according to the invention.

Skin-active vitamins, such as vitamins A, E and F, may be admixed with the foam skin cream according to the invention in effective amounts. Especially for the treatment and prevention of diaper dermatitis, admixing the following substances has proven useful: from 3 to 7% by weight of Calendula extract, from 3 to 7% by weight of Hamamelis extract, from 3 to 7% by weight of chamomile extract, from 3 to 7% by weight of tea tree oil extract, from 1 to 5% by weight of decyl oleate, from 1 to 5% by weight of octyl-dodecanol.

The process according to the invention for the preparation of the foam skin protection cream according to the invention comprises the following steps:

preparing a phase I by melting at 75° C. a mixture containing fatty acids, especially $C_{12}$–$C_{22}$ fatty acids, optionally unsaturated and/or polyunsaturated fatty acids, coemulsifiers, such as triceteareth-4-phosphate, followed by metering this phase with stirring to a phase II molten at 75° C. obtained from an aqueous mixture containing moisturizers, such as propylene glycol and/or polyhydric alcohols, especially glycerol, emulsifiers, such as alkyl sarcosinates, and skin care additives, such as allantoin, wherein homogeneous mixing of phases I and II is provided and said metering is performed at a temperature of 75° C.;

after the addition of phase I to phase II, the temperature is maintained at 75° C. for a period of between 5 and 20 minutes; whereupon the temperature of the thus obtained mixture is lowered to a temperature of between 30 and 40° C. with constant stirring;

adjusting the pH value to from 7.6 to 8.2, preferably with a skin-compatible basic organic compound, and filling into containers with the addition of a propellant.

The invention will be further illustrated by the following Example.

EXAMPLE

The skin protection cream according to the invention is prepared in a heatable and coolable closed apparatus with a self-withdrawing homogenisator and a heatable metering funnel (preferably in a Koruma multipurpose apparatus).

The preparation of phase I is effected in a heatable metering funnel by melting at 75° C. a mixture containing 2% by weight of glyceryl stearate, 4% by weight of cetearyl alcohol, 5% by weight of stearic acid, 1% by weight of paraffin and 1% by weight of triceteareth-4-phosphate, followed by metering this phase with stirring to phase II previously prepared in the heatable and coolable closed apparatus with a self-withdrawing homogenisator. Phase II consists of an aqueous mixture containing 2.5% by weight of propylene glycol, 2.5% by weight of glycerol, 2% by weight of sodium lauroylsarcosinate and 0.3% by weight of allantoin. The amount of water is 79.7% by weight. Homogeneous mixing of phases I and II is to be provided.

The metering of phase I is performed at a temperature of 75° C. Both phases are combined with constant stirring at a medium stirring speed, and care must be taken that homogenization is effected uniformly. The temperature is maintained at 75° C. for between 5 and 20 min. The mixture obtained is cooled to a temperature of between 30 and 40° C. with constant stirring.

Then, after a temperature of 40° C. has been reached, the further substances may be added. This may include adjusting the pH value to between 7.8 and 8.0. For this purpose, 2-amino-2-methyl-1-propanol is used. Stirring is continued for a sufficient period of time until the pH value has stabilized, followed by filling into suitable storage tanks or into the corresponding spraying containers. In the latter case, 91% of drug is filled together with 9% of butane/propane.

I claim:

1. A foam skin cream, wherein the skin cream does not contain PTFE, obtainable by preparing a phase I by melting at 75° C. a mixture containing fatty acids, optionally unsaturated and/or polyunsaturated fatty acids, emulsifiers, coemulsifiers, followed by metering it with stirring to a phase II temperature-controlled at 75° C. obtained from an aqueous mixture containing moisturizers, and/or emulsifiers, and/or skin care additives;

wherein homogeneous mixing of phases I and II is provided and said metering is performed at a temperature of 75° C.;

after the metered addition, the temperature is maintained at 75° C. for a period of between 5 and 20 minutes; whereupon the temperature of the thus obtained mixture is lowered to a temperature of between 30 and 40° C. with constant stirring;

the pH value is adjusted to from 7.6 to 8.2, and the mixture obtained is filled into dosage forms with the addition of a propellant;

the foam skin cream containing from 1 to 3% by weight of glyceryl stearate;
from 3 to 6% by weight of cetearyl alcohol;
from 4 to 6% by weight of stearic acid;
from 0.5 to 2% by weight of paraffin;
from 0.4 to 2.3% by weight of triceteareth-4-phosphate;
from 1.5 to 4% by weight of propylene glycol;
from 1.3 to 4.2% by weight of glycerol;
from 1 to 3% by weight of cetyl sarcosinate;
from 0.05 to 1% by weight of allantoin; and
water as the balance to make 100% by weight.

2. The foam skin cream according to claim 1, additionally containing a silicone-containing compound in phase I.

3. The foam skin cream according to claim 1, additionally containing one or more refatting substances in phase I.

4. The foam skin cream according to claim 3, containing from 0.5 to 2% by weight of decyl oleate; and/or from 0.5 to 2% by weight of octyldecanol.

5. The foam skin cream according to claim 3, containing from 3 to 6% by weight of decyl oleate; and/or from 3 to 6% by weight of octyldecanol.

6. The foam skin cream according to claim 3, containing from 6 to 9% by weight of decyl oleate; and/or from 6 to 9% by weight of octyldecanol.

7. The foam skin cream according to claim 1, additionally containing moisture-binding agents in phase HIII.

8. The foam skin cream according to claim 1, containing polyunsaturated fatty acids and/or vitamins.

9. The foam skin cream according to claim 2, containing
from 3 to 7% by weight of Calendula extract;
from 3 to 7% by weight of Hamamelis extract;
from 3 to 7% by weight of chamomile extract;
from 3 to 7% by weight of tea tree oil extract;
from 1 to 5% by weight of decyl oleate;
from 1 to 5% by weight of octyldodecanol.

10. The foam skin cream according to claim 1, wherein the fatty acids in phase I are $C_{12}$–$C_{22}$ fatty acids.

11. The foam skin cream according to claim 1, wherein the coemulsifier in phase I is triceteareth-4-phosphate.

12. The foam skin cream according to claim 1, wherein the moisturizers in phase II are propylene glycol and/or polyhydric alcohols.

13. The foam skin cream according to claim 1, wherein the moisturizers in phase II is glycerol.

14. The foam skin cream according to claim 1, wherein the emulsifiers in phase II are alkyl sarcosinates.

15. The foam skin cream according to claim 1, wherein the skin care additives in phase II are allantoin.

16. The foam skin cream according to claim 1, wherein the pH value is adjusted to from 7.6 to 8.2 with a skin-compatible basic organic compound.

17. The foam skin cream according to claim 2, wherein the silicone-containing compound is dimethicone.

18. The foam skin cream according to claim 2, wherein the silicone-containing compound is dimethicone in amounts of from 0.05 to 1% by weight.

19. The foam skin cream according to claim 3, wherein the refatting substances are decyl oleate, isohexadecane, stearic acid glycol ester, coconut fatty acid ethanolamide, corn oil, peanut oil, almond oil, sesame oil, olive oil, jojoba oil, soybean oil, wool wax alcohols, paraffin, medium-chain triglycerides, oleic acid oleyl esters, white petrolatum, macrogolglycerol hydroxystearate, hydrogenated castor oil, castor oil from *Ricinus communis*, avocado oil, wheat germ oil, palmitic acid isopropyl ester, cetly palmitate, myristic acid myristyl ester and/or octyldodecanol.

20. The foam skin cream according to claim 7, wherein the hydratizing agents are urea, ethoxydiglycol, sodium chloride, magnesium chloride, sorbitol, dexpanthenol, sodium lactate.

21. The foam skin cream according to claim 7, wherein the moisture-binding agent is from 1 to 20% by weight of urea.

22. The foam skin cream according to claim 8, wherein the polyunsaturated fatty acids are ω-6 fatty acids.

23. The foam skin cream according to claim 8, further containing chamomile extract.

* * * * *